(12) United States Patent
Gallagher et al.

(10) Patent No.: US 11,332,442 B2
(45) Date of Patent: May 17, 2022

(54) SYNTHETIC PROCESS

(71) Applicant: BRISTOL-MYERS SQUIBB COMPANY, Princeton, NJ (US)

(72) Inventors: William P. Gallagher, Clarksburg, NJ (US); John Ryan Coombs, Tinton Falls, NJ (US); Carlos A. Guerrero, North Wales, PA (US); David Marcoux, Pennington, NJ (US); Qing Shi, Princeton, NJ (US); Candice Lee Joe, Metuchen, NJ (US); Sanjeewa Rupasinghe, Pennington, NJ (US); Jason J. Zhu, East Brunswick, NJ (US); Srinivas Kalidindi, Bangalore (IN); Sathasivam Shunmugaraj, Hosur (IN); Moorthy Kandasamy, Tiruvannamalai (IN); Siva Sankar Bondigela, Bangalore (IN); Rajappa Vaidyanathan, Bangalore (IN); Shankar Tulsidas Tendulkar, Uttara Kannada (IN); Sankar Kuppusamy, Cuddalore District (IN); Francisco González-Bobes, Hillsborough, NJ (US)

(73) Assignees: Bristol-Myers Squibb Company, Princeton, NJ (US); Syngene International Limited, Karnataka (IN)

( * ) Notice: Subject to any disclaimer, the term of this patent is extended or adjusted under 35 U.S.C. 154(b) by 0 days.

(21) Appl. No.: 16/991,357

(22) Filed: Aug. 12, 2020

(65) Prior Publication Data

US 2022/0048859 A1    Feb. 17, 2022

(51) Int. Cl.
| | | |
|---|---|---|
| *C07D 209/60* | (2006.01) | |
| *C07C 315/04* | (2006.01) | |
| *C07C 303/40* | (2006.01) | |
| *C07C 311/03* | (2006.01) | |
| *C07C 317/24* | (2006.01) | |

(52) U.S. Cl.
CPC .......... *C07D 209/60* (2013.01); *C07C 303/40* (2013.01); *C07C 315/04* (2013.01); *C07C 311/03* (2013.01); *C07C 317/24* (2013.01)

(58) Field of Classification Search
None
See application file for complete search history.

(56) References Cited

U.S. PATENT DOCUMENTS 9,815,859 B2    11/2017  Duan et al.

OTHER PUBLICATIONS

Hodgson et al. "Terminal Aziridines by α-Deprotonation/Electrophile Trapping of N-Protected Aziridine" Organic Letters, 2008, vol. 10, No. 16, pp. 3453-3456.*

* cited by examiner

*Primary Examiner* — Joseph R Kosack
(74) *Attorney, Agent, or Firm* — Elliott Korsen; Shrikant M. Kulkarni

(57) ABSTRACT

The invention generally relates to a process for preparing compounds, including Compound of Formula (I), useful as key intermediates in the preparation of compounds having RORγt antagonist properties.

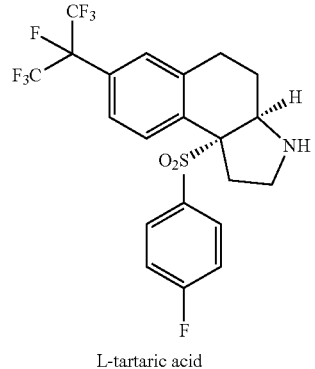

Compound of Formula (I)

L-tartaric acid

4 Claims, No Drawings

SYNTHETIC PROCESS

FIELD OF THE INVENTION

The invention generally relates to a process for preparing compounds useful as RORγt antagonists.

BACKGROUND OF THE INVENTION

Retinoic acid-related orphan receptor gamma (RORγt) plays a critical role in the differentiation and proliferation of Th17 cells, and is a target of interest for treating autoimmune diseases. International Patent Application WO 2016/179460 discloses several compounds that may be useful in the treatment of auto-immune and auto-inflammatory diseases such as psoriasis, rheumatoid arthritis, inflammatory bowel disease, Crohn's disease, ulcerative colitis, acute graft-versus-host disease, psoriatic arthritis, ankylosing spondylitis and multiple sclerosis. The invention provides an improved process for the preparation of Compounds of Formula (I), (II) and (III), which are useful as key intermediates in the preparation of some of the compounds disclosed in WO 2016/179460, such as compounds according to examples 831 and 832.

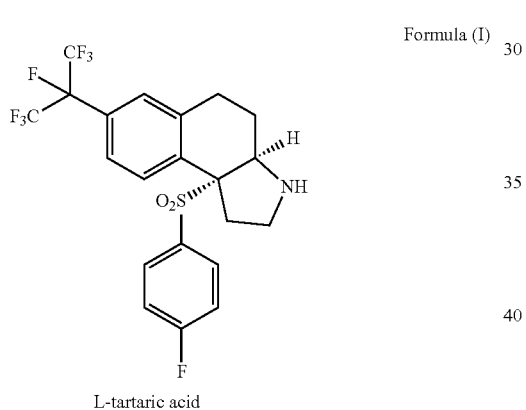

Formula (I)

L-tartaric acid

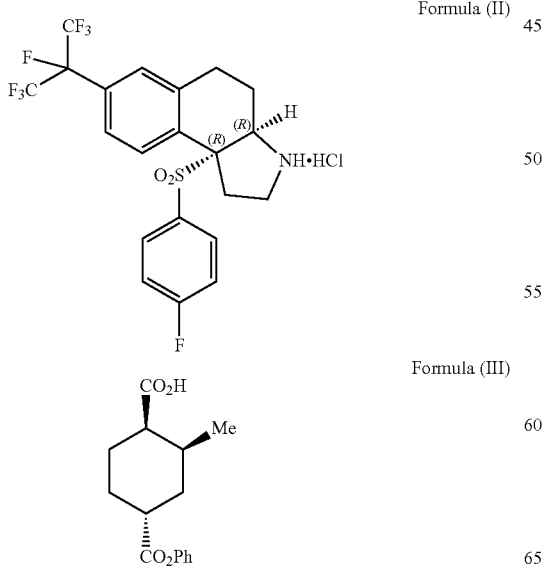

Formula (II)

Formula (III)

SUMMARY OF THE INVENTION

In a first aspect, the invention provides a process for the preparation of a Compound of Formula (I):

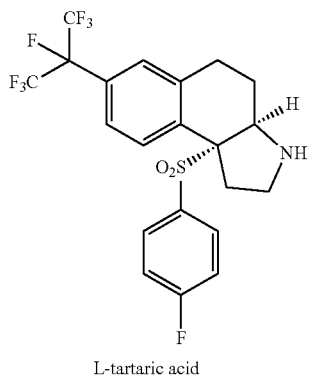

Compound of Formula (I)

L-tartaric acid comprising the steps of (a) reacting Compound 1 of the formula,

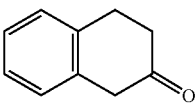

Compound 1 with 4-fluorobenzenesulfinic acid in the presence of 1-methyl-2-pyrrolidinone and iodine to afford Compound 2 of the formula, Compound 2

(b) reacting Compound 2 with heptafluoroisopropyl iodide in the presence of a base to afford Compound 3 of the formula,

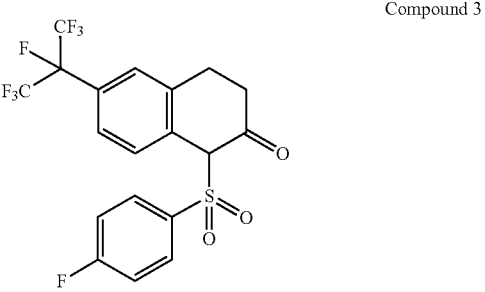 [SMILES: O=C1CCc2cc(C(F)(C(F)(F)F)C(F)(F)F)ccc2C1S(=O)(=O)c1ccc(F)cc1]

Compound 3

(c) reacting Compound 3 with a reducing agent to afford Compound 4 of the formula,

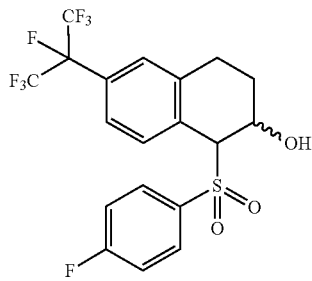

Compound 4

(d) reacting Compound 4 with trifluoroacetic anhydride and sodium t-pentoxide in the presence of 2-methyltetrahydrofuran to afford Compound 5 of the formula,

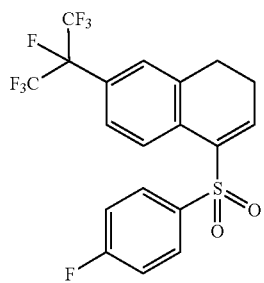

Compound 5

(e) reacting Compound 5 with Compound 6 of the formula,

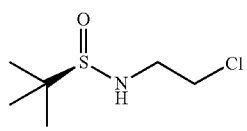

Compound 6 in the presence of sodium t-pentoxide to afford Compound 7 of the formula,

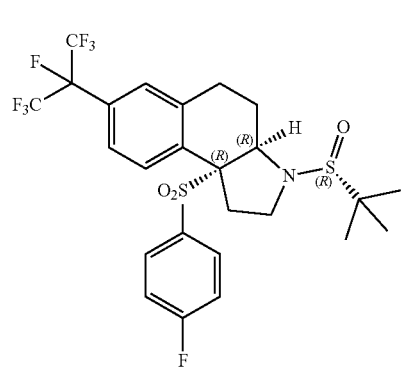

Compound 7

(f) reacting Compound 7 with chlorotrimethylsilane, followed by L-(+)-tartaric acid to afford the Compound of Formula (I).

In a second aspect, the invention provides a process for the preparation of a Compound of Formula (II):

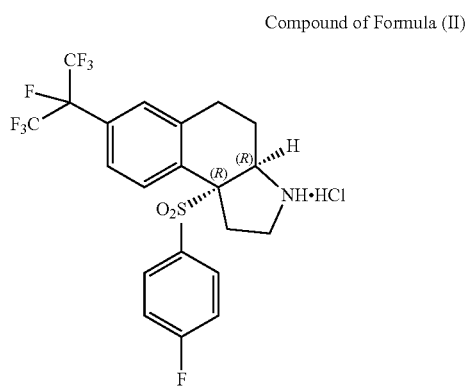

Compound of Formula (II)

comprising the steps of (a) reacting Compound 8 of the formula,

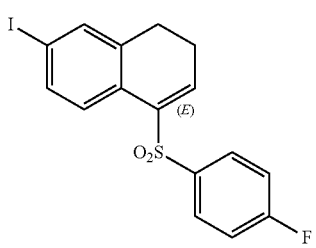

Compound 8 with Compound 6 in the presence of sodium t-pentoxide and tetrahydrofuran to afford Compound 9 of the formula

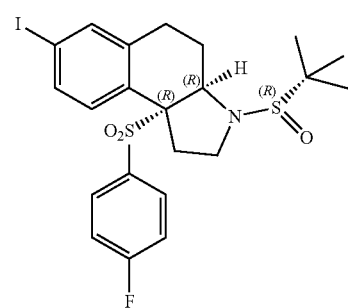

Compound 9

(b) reacting Compound 9 with chlorotrimethylsilane in the presence of a suitable solvent to afford Compound 10 of the formula,

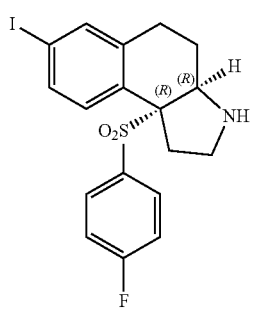

Compound 10

(c) reacting Compound 10 with di-tert-butyl dicarbonate (Boc$_2$O) in the presence of a base to afford Compound 11 of the formula,

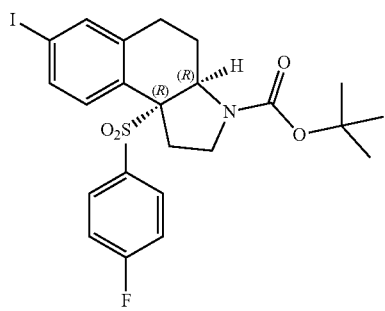

Compound 11

(d) reacting Compound 11 with iPrMgCl in the presence of carbon dioxide and tetrahydrofuran to afford Compound 12 of the formula,

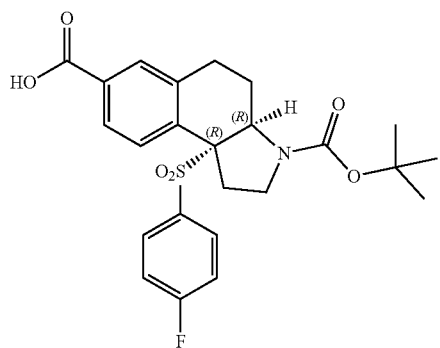

Compound 12

(e) reacting Compound 12 with trifluoromethyltrimethylsilane and N,N'-carbonyldiimidazole in the presence of dichloromethane to obtain Compound 13 of the formula,

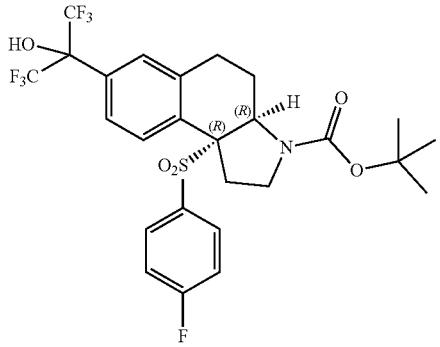

Compound 13

(f) reacting Compound 13 with a fluorinating agent to obtain Compound 14 of the formula,

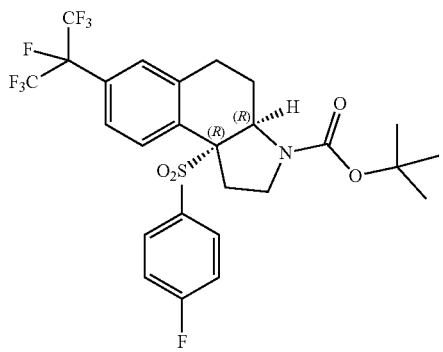

Compound 14

(g) reacting Compound 14 with HCl in dioxane to obtain the Compound of Formula (II).

In a third aspect, the invention provides a process for the preparation of a Compound of Formula (III):

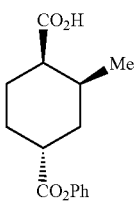

Compound of Formula (III)

comprising the steps of (a) converting Compound 15 of the formula,

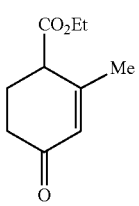

Compound 15 into Compound 16 of the formula,

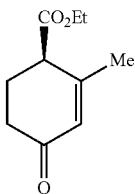

Compound 16

(b) hydrogenating Compound 16 to afford Compound 17 of the formula,

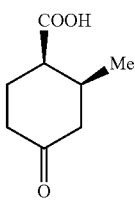

Compound 17

(c) reacting Compound 17 with trifluoroacetic anhydride and t-butanol to afford Compound 18 of the formula,

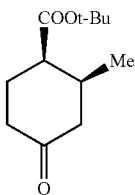

Compound 18

(d) reacting Compound 18 with a suitable reagent to afford a mixture of Compounds 19a and 19b of the formulae,

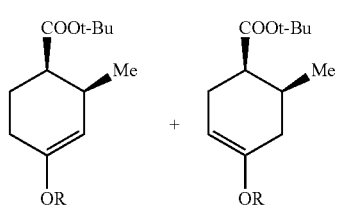

Compounds 19a and 19b wherein R is tosyl (Ts), mesyl (Ms), triflyl (Tf), and nonafluorobutanesulfonyl or perfluorobutanesulfonyl (Nf).

(e) reacting the mixture of Compounds 19a and 19b with phenol in the presence of N,N-diisopropylethylamine followed reaction with Pd(OAc)$_2$ and 4,5-bis(diphenylphosphino)-9,9-dimethylxanthene in the presence of carbon monoxide to afford a mixture of Compounds 20a and 20b of the formulae,

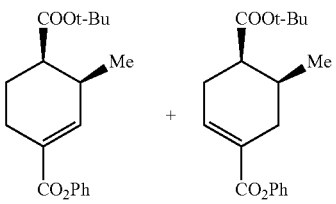

Compounds 20a and 20b (f) reacting the mixture of Compounds 20a and 20b with trifluoroacetic acid in the presence of dichloromethane to afford a mixture of Compounds 21a and 21b of the formulae,

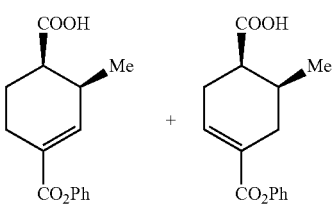

Compounds 21a and 21b (g) reacting the mixture of Compounds 21a and 21b with a hydrogenating agent to afford the Compound of Formula (III).

In a fourth aspect, the invention provides Compound 6 of the formula,

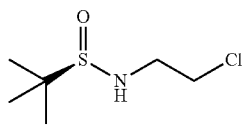

and a process for the preparation thereof.

The processes of the invention have several important advantages over prior syntheses of these compounds. In particular, due to the short sequence of chemical steps, high yields and process improvements, the throughput, cycle-time, and overall yields have improved. Additionally, the processes consistently provide these compounds in high quality for use as active pharmaceutical ingredient (API). The details of one or more embodiments of the invention are set forth in the description below. features, objects and advantages of the invention will be apparent from the following description including claims.

DETAILED DESCRIPTION OF THE INVENTION

The invention will now be further described with the following working example(s), which are preferred embodiments of the invention. One or more reactions according to the invention may be carried out one after the other without isolating the individual products (telescopic reaction). A person skilled in the art will appreciate that a variety of reagents may be used in place of the described reagents to achieve the desired chemical transformations. A reference to any of the compounds described herein also includes their salts. All temperatures are in degrees Celsius (° C.) unless otherwise indicated. These examples are illustrative rather than limiting and it is to be understood that there may be other embodiments that fall within the spirit and scope of the invention as defined by the claims appended hereto. All references including patents, patent applications, and literature cited in the specification are expressly incorporated herein by reference in their entirety as if fully rewritten herein. For ease of reference, the following abbreviations are used herein.

| Abbreviations | Name |
|---|---|
| AcOH | Acetic acid |
| ACN | Acetonitrile |
| aq. | Aqueous |
| Conc. | Concentrated |
| CO | Carbon monoxide |
| $CO_2$ | Carbon dioxide |
| CsF | Cesium fluoride |
| $Boc_2O$ | Di-tert-butyl dicarbonate |
| t-BuOH | tert-Butanol |
| CDI | N,N'-carbonyldiimidazole |
| DCM | Dichloromethane |
| DIPEA | N,N-diisopropylethylamine |
| EtOAc | Ethyl acetate |
| Eq. | Equivalents |
| H | Hours |
| HCl | Hydrochloric acid |
| HPLC | High pressure liquid chromatography |
| IPA | Isopropanol |
| Me | Methyl |
| MeOH | Methanol |
| MTBE | Methyl t-butyl ether |
| NaOH | Sodium Hydroxide |
| NLT | Not less than |
| NMT | Not more than |
| PhMe | Toluene |
| rt/RT | Room temperature |
| t-pentoxide | tert-pentoxide |
| $NaBH_4$ | Sodium borohydride |
| NMP | 1-methyl-2-pyrrolidinone |
| Pd | Palladium |
| $Pd(OAc)_2$ | Palladium acetate |
| sat. | Saturated |
| Rh | Rhodium |
| TBAF | Tetrabutylammonium fluoride |
| TFA | Trifluoroacetic acid |
| TFAA | Trifluoroacetic anhydride |
| 2-Me-THF | 2-methyltetrahydrofuran |
| THF | Tetrahydrofuran |
| TMS | Chlorotrimethylsilane |
| $TMSCF_3$ | Trifluoromethyltrimethylsilane |
| $Ts_2O$ | p-Toluenesulfonic anhydride |
| XtalFluor-E | (Diethylamino) difluorosulfonium tetrafluoroborate |
| Xantphos | 4,5-Bis(diphenylphosphino)-9,9-dimethylxanthene |

Accordingly, there are provided improved processes for the preparation of Compounds of Formula (I), (II) and (III).

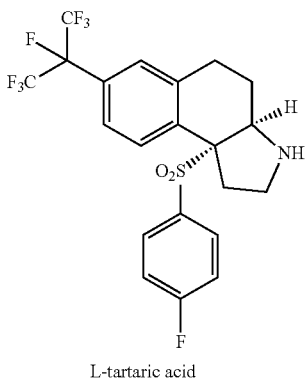

L-tartaric acid

Formula (I)

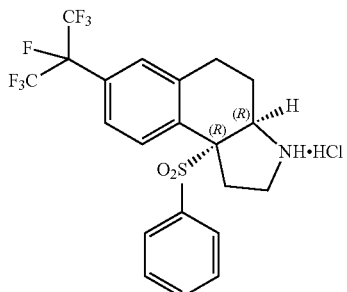

Formula (II)

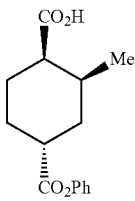

Formula (III)

Preparation of Compound of Formula (I)

The Compound of Formula (I) could be prepared starting from Compound 1 as follows. Compound 2 was obtained by reacting Compound 1 with 4-fluorobenzenesulfinic acid in the presence of 1-methyl-2-pyrrolidinone and iodine. Compound 3 was obtained by reacting Compound 2 with heptafluoroisopropyl iodide in the presence of a base. Typical, non-limiting examples of suitable bases include aqueous sodium hydroxide. The reaction may be carried out in the presence of such other reagents as tetrabutylammonium hydrogen sulfate, sodium hydrosulfite, and 2-methyltetrahydrofuran. Compound 4 was obtained by reacting Compound 3 with a reducing agent in the presence of a suitable solvent. Typical, non-limiting examples of such reducing agents include, sodium borohydride, lithium hydride, and hydrogen in the presence of metal hydrogenation catalysts comprising palladium, ruthenium, rhodium and the like. Compound 5 was obtained by reacting Compound 4 with trifluoroacetic anhydride and sodium t-pentoxide in the presence of a solvent such as 2-methyltetrahydrofuran. Compound 6 was obtained by reacting (R)-2-methylpropane-2-sulfinimide with chloroacetaldhyde in the presence of toluene, water and $CuSO_4$. Compound 7 was obtained by reacting Compound 5 with Compound 6 in the presence of sodium t-pentoxide in toluene. The Compound of Formula (I) was obtained by reacting Compound 7 with chlorotrimethylsilane, followed by L-(+)-tartaric acid.

In general, the process for preparation of Compound of Formula (I) is summarized in Scheme 1.

Scheme 1

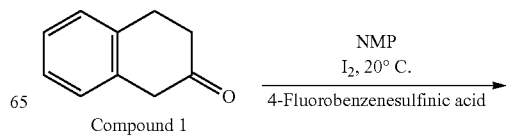

Compound 1

$\xrightarrow{\text{NMP} \\ I_2, 20°\text{ C.} \\ \text{4-Fluorobenzenesulfinic acid}}$

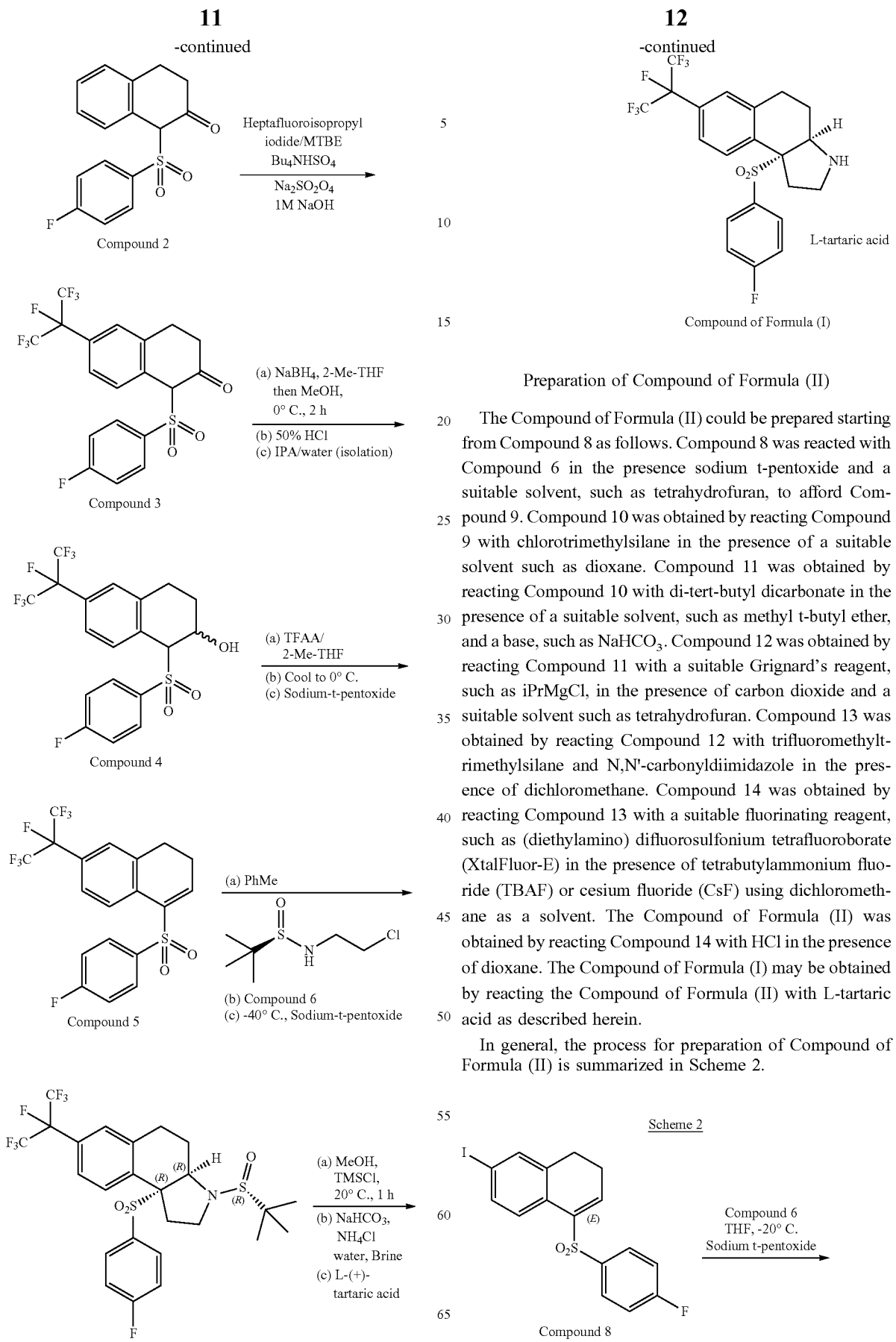

Preparation of Compound of Formula (II)

The Compound of Formula (II) could be prepared starting from Compound 8 as follows. Compound 8 was reacted with Compound 6 in the presence sodium t-pentoxide and a suitable solvent, such as tetrahydrofuran, to afford Compound 9. Compound 10 was obtained by reacting Compound 9 with chlorotrimethylsilane in the presence of a suitable solvent such as dioxane. Compound 11 was obtained by reacting Compound 10 with di-tert-butyl dicarbonate in the presence of a suitable solvent, such as methyl t-butyl ether, and a base, such as NaHCO$_3$. Compound 12 was obtained by reacting Compound 11 with a suitable Grignard's reagent, such as iPrMgCl, in the presence of carbon dioxide and a suitable solvent such as tetrahydrofuran. Compound 13 was obtained by reacting Compound 12 with trifluoromethyltrimethylsilane and N,N'-carbonyldiimidazole in the presence of dichloromethane. Compound 14 was obtained by reacting Compound 13 with a suitable fluorinating reagent, such as (diethylamino) difluorosulfonium tetrafluoroborate (XtalFluor-E) in the presence of tetrabutylammonium fluoride (TBAF) or cesium fluoride (CsF) using dichloromethane as a solvent. The Compound of Formula (II) was obtained by reacting Compound 14 with HCl in the presence of dioxane. The Compound of Formula (I) may be obtained by reacting the Compound of Formula (II) with L-tartaric acid as described herein.

In general, the process for preparation of Compound of Formula (II) is summarized in Scheme 2.

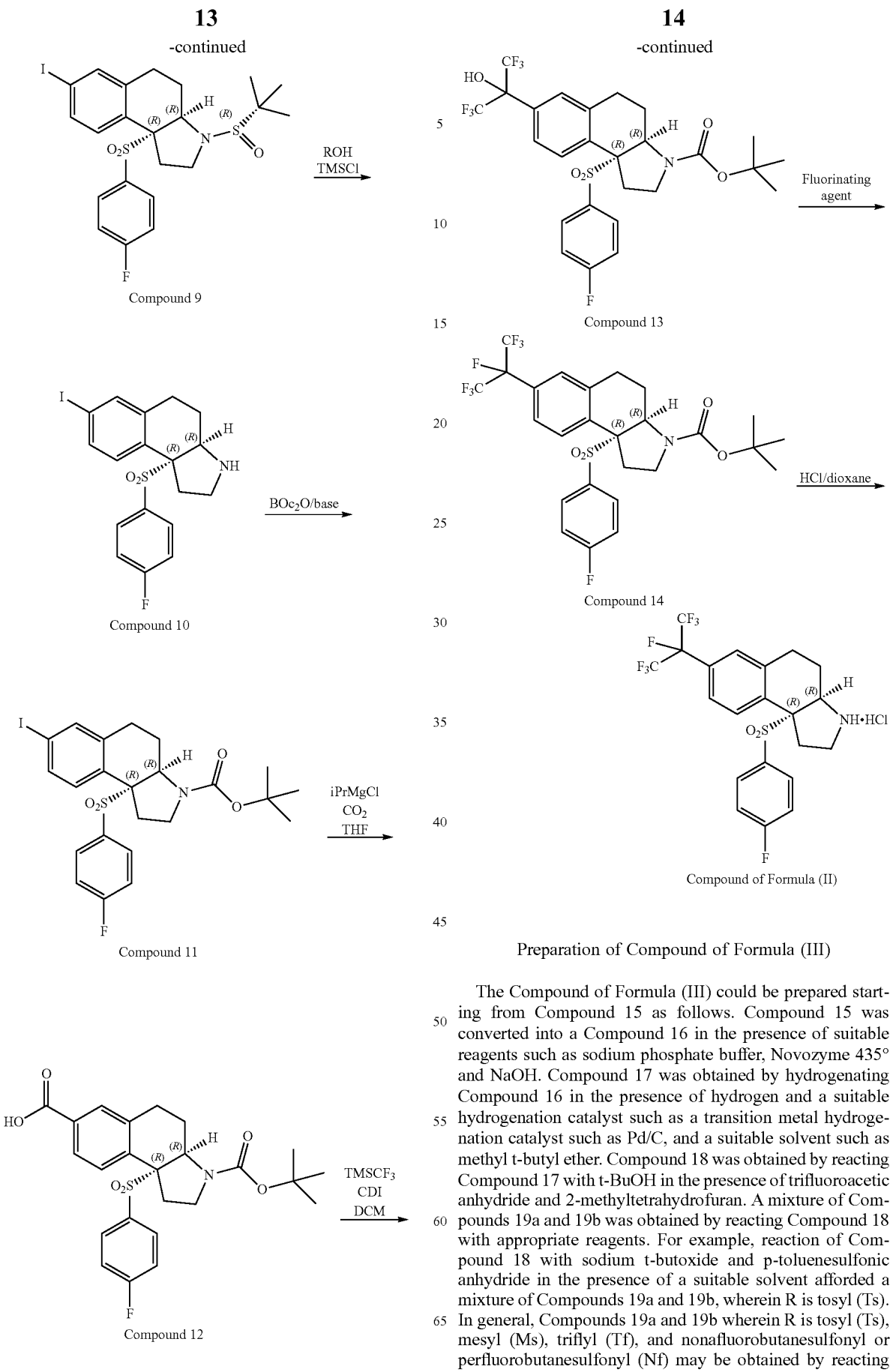

Preparation of Compound of Formula (III)

The Compound of Formula (III) could be prepared starting from Compound 15 as follows. Compound 15 was converted into a Compound 16 in the presence of suitable reagents such as sodium phosphate buffer, Novozyme 435° and NaOH. Compound 17 was obtained by hydrogenating Compound 16 in the presence of hydrogen and a suitable hydrogenation catalyst such as a transition metal hydrogenation catalyst such as Pd/C, and a suitable solvent such as methyl t-butyl ether. Compound 18 was obtained by reacting Compound 17 with t-BuOH in the presence of trifluoroacetic anhydride and 2-methyltetrahydrofuran. A mixture of Compounds 19a and 19b was obtained by reacting Compound 18 with appropriate reagents. For example, reaction of Compound 18 with sodium t-butoxide and p-toluenesulfonic anhydride in the presence of a suitable solvent afforded a mixture of Compounds 19a and 19b, wherein R is tosyl (Ts). In general, Compounds 19a and 19b wherein R is tosyl (Ts), mesyl (Ms), triflyl (Tf), and nonafluorobutanesulfonyl or perfluorobutanesulfonyl (Nf) may be obtained by reacting Compound 18 with p-toluenesulfonic anhydride, methanesulfonic anhydride, trifluoromethanesulfonic or triflic anhydride, and perfluorobutanesulfonyl or nonafluorobutanesulfonyl fluoride respectively, in presence of appropriate reaction conditions.

A mixture of Compounds 20a and 20b was obtained by reacting the mixture of Compounds 19a and 19b with carbon monoxide in the presence of phenol, N,N-diisopropylethylamine, Pd(OAc)$_2$ and 1,3-bis(diphenylphosphino)propane. A mixture Compounds 21a and 21b was obtained by reacting the mixture of Compounds 20a and 20b with trifluoroacetic acid in the presence of dichloromethane. The Compound of Formula (III) was obtained by hydrogenating the mixture of Compounds 21a and 21b in the presence of a suitable catalyst and a solvent, for example, hydrogen in presence of bis(1,5-cyclooctadiene)rhodium(I) tetrafluoroborate, 1,1'-Bis-(dicyclohexylphosphino) ferrocene in the presence of ethyl acetate.

In general, the process for preparation of Compound of Formula (III) is summarized in Scheme 3.

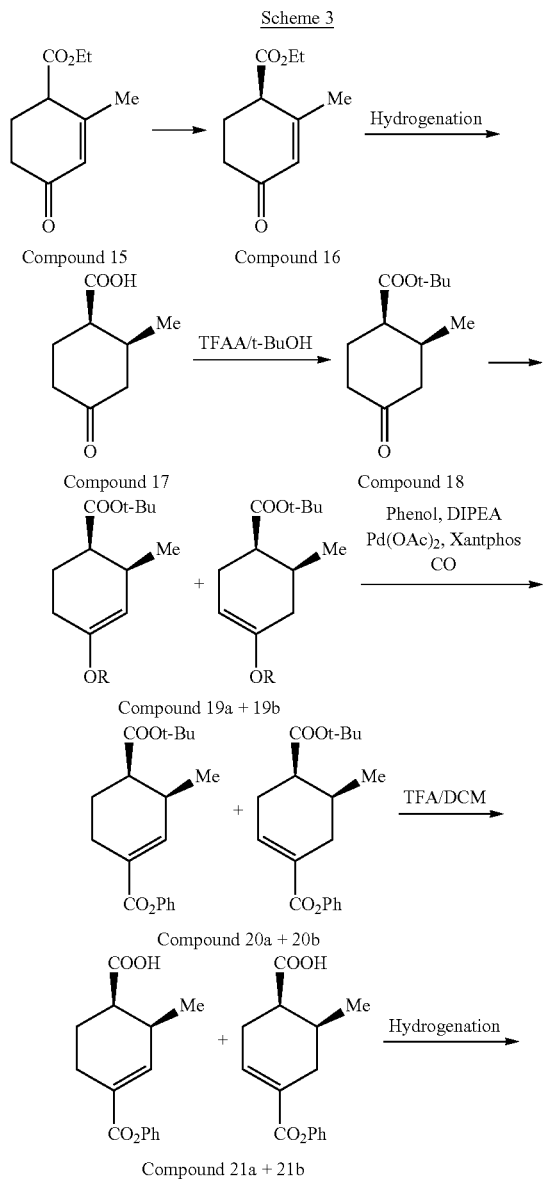

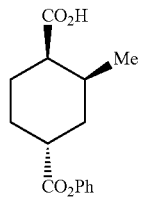

Compound of Formula (III)

Preparation of Compound 6

Compound 6 of formula,

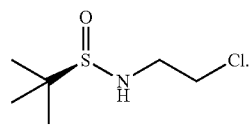

Compound 6 could be obtained by (a) reacting (R)-2-methylpropane-2-sulfinimide with chloroacetaldhyde in presence of toluene, water and CuSO$_4$, and (b) reacting the reaction mixture of step (a) above with sodium borohydride followed by recovering the Compound 6.

EXPERIMENTAL SECTION

General

All reactions were performed under a nitrogen atmosphere using anhydrous techniques unless otherwise noted. All temperatures are in degrees Celsius (° C.) unless otherwise indicated. Reagents were used as received from the vendors, unless otherwise noted. Quoted yields are for isolated material, and not corrected for moisture content. Reactions were monitored by GC or reverse phase HPLC on a Shimadzu system using CH$_3$CN/H$_2$O/MeOH as the mobile phase (containing either 0.05% TFA, or 0.1% NH$_4$OAc). Melting points were recorded using a Thomas Hoover melting point apparatus and are uncorrected. The quantitative analysis of residual palladium catalyst was performed with a Perkin-Elmer Optima 4300 DV ICP-AES instrument.

Examples

The invention will now be further described by the following working example(s), which are preferred embodiments of the invention. These examples are illustrative rather than limiting and it is to be understood that there may be other embodiments that fall within the spirit and scope of the invention as defined by the claims appended hereto. All such alterations and further modifications of the inventive features illustrated herein, which would occur to one skilled in the relevant art and having possession of this disclosure, are to be considered within the scope of the invention. A person of skills in the art will appreciate that each of these reactions may be carried in presence of one or more solvents and suitable reaction conditions, and one or more steps may be combined together without isolating one or more intermediates.

Example 1

Preparation of Compound 2

1-Methyl-2-pyrrolidinone (8.04 kg), 4-fluorobenzenesulfinic acid (1.50 kg, 1.2 equiv.) and 2-tetralone (1.0 kg) were added to a reactor at 20° C. The reaction mixture was cooled to 15° C. and iodine (1.74 kg, 1.0 equiv.) was added in 4 equal portions maintaining the reaction mixture temperature at NMT 35° C. The reaction mixture was allowed to stir at 20° C. for NLT 2 h. On completion of the reaction, temperature of the reaction mixture was adjusted to 70° C. and water (8.0 kg) was added maintaining the temperature of the reaction mixture at NLT 65° C. On completion of the reaction, the reaction mixture was cooled to 20° C. and held at 20° C. for NLT 6 h. The solids thus obtained were filtered and washed with 2-propanol (6.3 kg) and then dried to afford Compound 2 (1.37 kg, 73% yield).

Example 2

Preparation of Compounds 3 and 4 in a Telescopic Fashion

Compound 2 (1.0 kg) and methyl t-butyl ether (5.33 kg) were added to a reactor followed by tetrabutylammonium hydrogen sulfate (0.078 kg, 0.070 equiv.), sodium hydrosulfite (0.83 kg, 1.45 equiv.), NaOH (10.4 L, 1.0 N aqueous solution) and heptafluoroisopropyl iodide (1.42 kg, 1.5 equiv.). The reactor was purged with nitrogen and the reaction mixture was allowed to stir at 20° C. for NLT 2 h. On completion of the reaction, the aqueous layer was removed and the reactor was charged with brine (8.33 kg). The reaction mixture was agitated and the aqueous layer was removed. Aqueous HCl (10.0 L, 6M solution) was added at 20° C. and the reaction mixture was held at 20° C. for NLT 3 h. The aqueous layer was removed and the organic layer was distilled to a minimum volume. After solvent swapping into 2-methyltetrahydrofuran (6.83 kg), the organic layer was polish filtered. The reaction mixture was cooled to −10° C. and NaBH$_4$ (0.22 kg, 1.80 equiv.) was charged into the reactor maintaining temperature of the reaction mixture at NMT 8° C. At −5° C., methanol (1.58 kg) was charged into the reactor to maintain the reaction mixture temperature at NMT 6° C. The reaction mixture was held at 0° C. for NLT 1 h. HCl (3.0 L, 6 M solution) and water (4.0 kg) were added at −5° C. The reaction mixture was then warmed to 20° C. and held for NMT 30 min. The aqueous layer was removed and the organics were washed with water (4.5 kg). The organics were solvent swapped into isopropanol (5.0 L/kg end point with NMT 4 wt % 2-methyltetrahydrofuran). The reaction mixture was heated to 75° C. and water (0.50 L) was added to keep the reaction mixture temperature at NLT 70° C. The reaction was cooled to 20° C. over a period of NLT 6 h. At 20° C., water (4.5 L) was added over 4.5 h. The slurry was held at 20° C. for NLT 10 h. The solids thus obtained were filtered, washed with IPA/water (1:1, 2.0 L), and dried to afford Compound 4 as a solid (1.14 kg, 74% yield).

Example 3

Preparation of Compound 6

Toluene (1.2 L) and (R)-2-methylpropane-2-sulfinimide (150 g, LR) were added to a reactor followed by chloroacetaldhyde (239 mL, 50 wt % in water, 1.5 equiv.) and CuSO$_4$ (613 g, 3.1 equiv.). The reaction mixture was allowed to stir at 20° C. for NLT 2 h. The solids were filtered and the organics were cooled to −5° C. Under a nitrogen purge, NaBH$_4$ (37.51 g, 0.80 equiv.) was added followed by methanol (155 mL, 3.1 equiv.), and the reaction mixture was heated to 35° C. and held for NLT 12 h. The organics were washed with sat. aq. NH$_4$Cl (750 mL, 2×) and Brine (750 mL), followed by addition of activated carbon (225 g) and the resulting slurry was aged for NLT 30 min. The solids thus obtained were filtered and washed with toluene (750 mL). The organics were concentrated to a minimum volume and heptane (1.2 L) was added. This was repeated until there was NMT 1 wt % Toluene. The reaction mixture was cooled to −5° C. and aged for NLT 3 h. The solids were filtered, washed with heptane and dried to afford Compound 6 of as a solid (175 g, 76% yield).

Example 4

Preparation of Compound of Formula (I) in a Telescopic Fashion

Compound 4 (100 g) and 2-methyltetrahydrofuran (1.20 L) were added to a reactor and the reaction mixture was held at 20° C., followed by addition of trifluoroacetic anhydride (59.77 g, 1.35 equiv.) at 20° C., and the reaction mixture was held for NMT 30 min. On completion of the reaction, the reaction mixture was cooled to −5° C., followed by addition of sodium t-pentoxide (145 mL, 40 wt % in toluene) maintaining the temperature at NMT 10° C. After the addition, the reaction mixture was cooled to 0° C. and held for NMT 30 min. On completion of the reaction, Compound 6 (59.27 g, 1.5 equiv.) was added and the reaction mixture was cooled to −45° C., followed by addition of sodium t-pentoxide (110 mL, 40 wt % in PhMe) maintaining the temperature at NMT −40° C., and the mixture was held at −40° C. for NLT 1 h. On completion of the reaction, saturated aq. NH$_4$CL (500 mL) was added to the reaction mixture and the contents were warmed to 20° C. The aqueous layer was removed, and methanol (85 mL, 10 equiv.) and chlorotrimethylsilane (69 g, 3.0 equiv.) were added. The reaction mixture was held at 20° C. for NLT 1 h. On completion of the reaction, the organics were washed with aq. NaHCO$_3$ (1.03 L, 6.0 equiv.), sat. aq. NH$_4$Cl (1.0 L), water (500 mL) and then with brine (500 mL), followed by heating the reaction mixture to 55° C. To this reaction mixture, a solution of [L-(+)-tartaric acid (47.5 g, 1.5 equiv.), tetrahydrofuran (400 mL), and water (25 mL)] were added at 60° C. over a period of NLT 1 h. The slurry thus obtained was held at 60° C. for NLT 12 h. On completion of the reaction, the reaction mixture was cooled to 20° C. and held at 20° C. for NLT 3 h. The solids thus obtained were filtered, washed with tetrahydrofuran (600 mL) and dried to afford the Compound of Formula (I) as a solid (107 g, 78% yield).

Example 5

Preparation of Compound 17

Compound 15 (1.0 kg, 1.0 equiv.), sodium phosphate buffer (10 L, pH 7.0), and Novozyme 435 (200 g, 0.20 g/g·LR) were added to a reactor, and pH of the reaction mixture was maintained at 7 using an automatic titrator (5 N NaOH, total of ~1.1 L of 5 N NaOH used). On completion of the reaction, pH of the reaction mixture was adjusted to 8.5 with NaOH (10 N) and methyl t-butyl ether (5 L) was added to the reaction mixture and the contents were allowed to age for NLT 1 h at 20° C. The slurry thus obtained was filtered through celite and the cake obtained was washed with water (1.5 L). The organic layer was removed and pH of the aqueous layer was adjusted to 7 with conc. HCl. The aqueous phase was charged into a hydrogenation vessel along with Pd—Pb/CaCO$_3$ (50 g). The reactor was sealed and purged thrice with nitrogen (30 psi), followed by thrice with hydrogen (30 psi). The reaction mixture was maintained at hydrogen atmosphere (30 psi of hydrogen) until the reaction was complete. On completion of the reaction, the organics were treated with activated charcoal (200 g) and the contents were held at 20° C. for NLT 1 h. The solids thus obtained were filtered and the cake was washed with water (2 L). pH of the aqueous layer was adjusted to 7 with conc. HCl, and extracted with 2-methyltetrahydrofuran (5 L, 4×). The combined organics were washed with Brine (2.0 L), and concentrated to ~3 L, followed by addition of heptane. This was repeated until there was NMT 2 vol % methyl t-butyl ether and 2-methyltetrahydrofuran present. Ethyl acetate (1 L) was added to the reaction mixture and the slurry thus obtained was heated to 60° C., and then cooled to 20° C. over a period of NLT 12 h. The solids thus obtained were filtered, washed with 10% ethyl acetate/heptane (1.0 L) and dried to afford Compound 17 (75% yield) as a white solid.

Example 6

Preparation of Compound 18

Compound 17 (1.0 kg) and 2-methyltetrahydrofuran (20 L) were added to a reactor. The solution thus obtained was cooled to 0° C. and trifluoroacetic anhydride (1.48 kg, 1.1 eq) was added maintaining the temperature at NMT 10° C., and the reaction mixture was then held at 0° C. for NLT 15 min. At 0° C., t-BuOH (1.42 kg, 3.0 equiv.) was added to the reaction mixture and the resulting solution was held at 0° C. for NLT 10 h. on completion of the reaction, the reaction mixture was added to a 2$^{nd}$ reactor at 0° C. containing NH$_4$OH (2.27 kg, 7.0 equiv.). After the addition, the resulting solution was held at 0° C. for NLT 30 min, followed by addition of and Na$_2$CO$_3$ (5.0 L, 10% aqueous solution). The reaction mixture was allowed to warm to 20° C. and the layers were separated. Aqueous layer was extracted thrice with methyl t-butyl ether (5.0 L). The combined organics were washed with brine (5.0 L) and concentrated to afford Compound 18 (90% yield) as a liquid.

Example 7

Preparation of Compounds 20a and 20b

Tetrahydrofuran (10.0 L), sodium t-butoxide (0.905 kg, 2.0 equiv.) and toluene (10.0 L) were added to reactor #1 and the resulting solution was cooled to −60° C., followed by addition of a solution of Compound 18 (1.0 kg) in tetrahydrofuran (10.0 L) maintaining the temperature of the reaction mixture to NMT −40° C. After the addition, the solution was aged at −60° C. for NLT 10 min. In the meantime, tetrahydrofuran (9.0 L), and p-toluenesulfonic anhydride (2.92 kg, 1.90 equiv.) were added to reactor #2 and the temperature of the reaction mixture was adjusted to −20° C. The contents of reactor #1 were then added into the contents of reactor #2 over a period of NLT 40 min while maintaining temperature of the reaction mixture at NMT −15° C., and the resulting solution was maintained at NMT −20° C. for NLT 1 h., followed aging at 20° C. for NLT 20 min. On completion of the reaction, water (5.5 L) was added and the reaction mixture was held for NLT 10 min. The layers were separated. The aqueous layer was removed and the organics were washed with sat. aq. NaHCO$_3$ (5.5 L) followed by water (5.5 L). The organics were concentrated to 2 L total volume at 40° C., followed by addition of toluene (10.0 L). The resulting solution was concentrated to 6.5 L, followed by addition of acetonitrile (6.5 L), Pd(OAc)$_2$ (0.0135 kg, 0.022 equiv.) and 1,3-bis(diphenylphosphino)propane (0.0281 kg, 0.025 equiv.) in the pressure vessel. The pressure vessel was purged with nitrogen followed by addition phenol (0.77 kg, 3.0 equiv.) and N,N-diisopropylethylamine (0.882 kg, 2.5 equiv.). The pressure vessel was purged thrice with carbon monoxide (15 psi), and the system was maintained under carbon monoxide atmosphere (15 psi) during the entire reaction duration. The temperature of the reaction was adjusted to 60° C. and held for NLT 16 h. On competition of the reaction, the organics were concentrated to a minimum volume, followed by addition of toluene (9.0 L). The organics were washed with water (5.0 L), 6M HCl (5.0 L), aq. N-acetylcysteine (1.1 kg+5.0 L water), aq. LiOH (0.50 kg+5.0 L water, 2×), water (5.0 L, 2×) and then the organics were treated with silica gel and filtered. The resulting solution was then solvent swapped into methanol (7.0 L total), and the resulting solution was heated to 55° C. followed by cooling to 20° C. over a period of NLT 1 h. Water (3.0 L) was added over NLT 30 min and the reaction mixture was held at 20° C. for NLT 12 h. The solids were filtered, washed with water (3.0 L) and dried to afford a mixture of Compounds 20a and 20b as a solid (75% yield).

Example 8

Preparation of Compounds 21a and 21b

A mixture of Compounds 20a and 20b in dichloromethane (475 mL) were added to a reactor, and the reaction mixture was maintained at 20° C. Trifluoroacetic acid (152 mL) was added and the reaction mixture was held at 20° C. for NLT 18 h. On completion of the reaction, the reaction mixture was concentrated to a minimum volume and heptane (950 mL) was added. This was repeated until there was NMT 1% dichloromethane. The slurry thus obtained was aged for NLT 2 ha t 20° C. The solids thus obtained were filtered, washed with heptane (665 mL) and dried to afford the mixture of Compounds 21a and 21b (75 g, 95% yield) as a solid.

Example 9

Preparation of Compound of Formula (III)

Bis(1,5-cyclooctadiene)rhodium(I) tetrafluoroborate (837 mg), 1,1'-Bis(dicyclohexylphosphino)ferrocene (1.32 g), 1,2-dichloroethane (140 mL), and ethyl acetate (70 mL) were added to a pressure vessel. The reaction mixture was held at 20° C. for NLT 30 min, and thereafter the mixture of Compounds 21a and 21b in (70 g) was added along with ethyl acetate (910 mL). The reaction vessel was purged with nitrogen (30 psi, 2×) and then hydrogen (50 psi, 3×). The reaction vessel then pressurized with hydrogen (150 psi) and held at 20° C. for NLT 18 h. On completion of the reaction, the reaction mixture was solvent swapped into acetonitrile and the total volume was adjusted to about 2.0 L. The solution was cooled to 20° C. and (1R, 2S)-(−)-2-Amino-1, 2-diphenylethanol (54.5 g) was added. The solution was heated to 65° C. and held for NLT 1 h. The slurry was cooled to 20° C., then filtered and washed with acetonitrile (280 mL, 2×). The solids thus obtained were dissolved into methyl t-butyl ether (1.40 L) and aq. $H_3PO_4$ (water (2.10 L+$H_3PO_4$ (154 mL)) was added. The solution was stirred for NLT 30 min and then the aqueous layer was removed. The organics were washed with water (700 mL, 3×) and brine (280 mL). The organics were concentrated to a minimum volume and heptane (700 mL) was added. This was repeated until there was NMT 0.01% methyl t-butyl ether. The solids thus obtained were filtered, washed with heptane, and dried to afford the Compound of Formula (III) (52 g, 73% yield) as a white solid.

We claim:

1. A process for the preparation of a Compound of Formula (I):

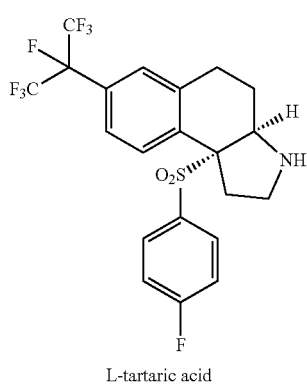

Compound of Formula (I)

L-tartaric acid comprising the steps of (a) reacting Compound 1 of the formula,

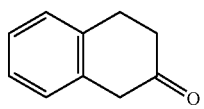

Compound 1 with 4-fluorobenzenesulfinic acid in the presence of 1-methyl-2-pyrrolidinone and iodine to afford Compound 2 of the formula,

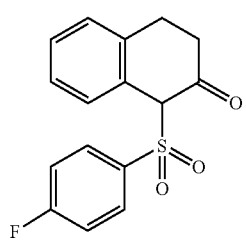

Compound 2

(b) reacting Compound 2 with heptafluoroisopropyl iodide in the presence of a base to afford Compound 3 of the formula,

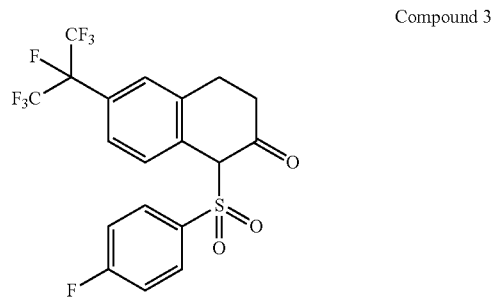 [SMILES: O=C1CCc2cc(C(F)(C(F)(F)F)C(F)(F)F)ccc2C1S(=O)(=O)c1ccc(F)cc1]

Compound 3

(c) reacting Compound 3 with a reducing agent to afford Compound 4 of the formula,

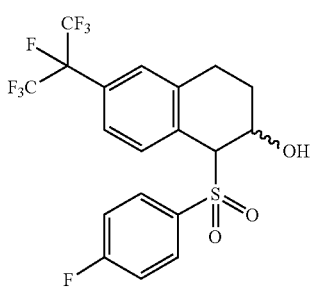

Compound 4

(d) reacting Compound 4 with trifluoroacetic anhydride and sodium t-pentoxide in the presence of 2-methyltetrahydrofuran to afford Compound 5 of the formula,

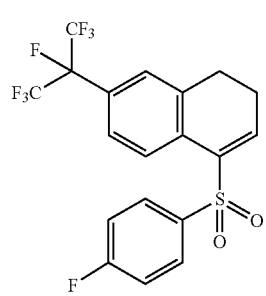

Compound 5

(e) reacting Compound 5 with Compound 6 of the formula,

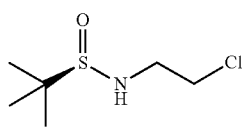

Compound 6 in the presence of sodium t-pentoxide to afford Compound 7 of the formula,

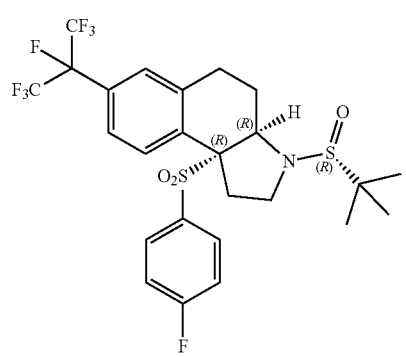

Compound 7

(f) reacting Compound 7 with chlorotrimethylsilane, followed by L-(+)-tartaric acid to afford the Compound of Formula (I).

2. The process according to claim 1, comprising the steps of (a) reacting Compound 1 with 4-fluorobenzenesulfinic acid in the presence of 1-methyl-2-pyrrolidinone and iodine to afford Compound 2, (b) reacting Compound 2 with heptafluoroisopropyl iodide in the presence of a base to afford Compound 3, (c) reducing Compound 3 with sodium borohydride in solvent to afford Compound 4, (d) reacting Compound 4 with trifluoroacetic anhydride and sodium t-pentoxide in the presence of 2-methyltetrahydrofuran to afford Compound 5, (e) reacting Compound 5 with Compound 6 in the presence of sodium t-pentoxide to afford Compound 7, and (f) reacting Compound 7 with chlorotrimethylsilane, followed by L-(+)-tartaric acid to afford the Compound of Formula (I).

3. A process for the preparation of a Compound of Formula (II):

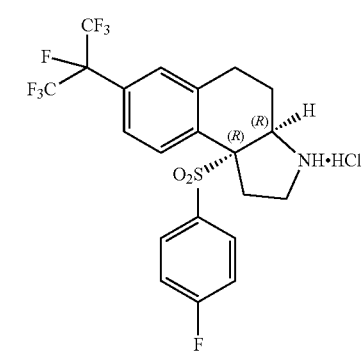

Compound of Formula (II)

comprising the steps of (a) reacting Compound 8 of the formula,

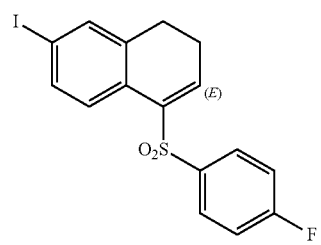

Compound 8 with Compound 6 of the formula,

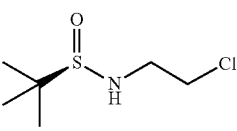

Compound 6 in the presence of sodium t-pentoxide and tetrahydrofuran to afford Compound 9 of the formula,

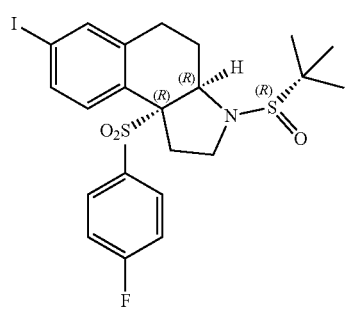

Compound 9

(b) reacting Compound 9 with chlorotrimethylsilane in the presence of a suitable solvent to afford Compound 10 of the formula,

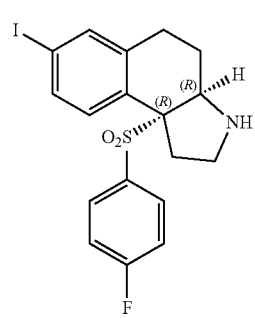

Compound 10

(c) reacting Compound 10 with di-tert-butyl dicarbonate (Boc₂O) in the presence of a base to afford Compound 11 of the formula, Compound 11

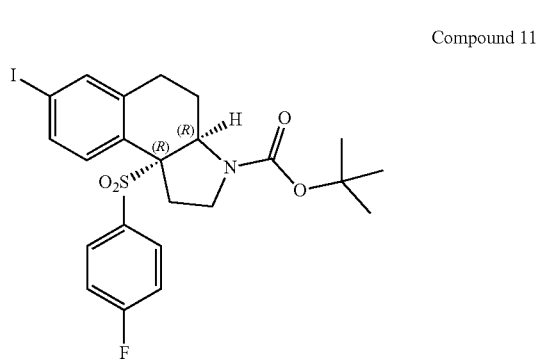

(d) reacting Compound 11 with iPrMgCl in the presence of CO₂ and tetrahydrofuran to afford Compound 12 of the formula, Compound 12

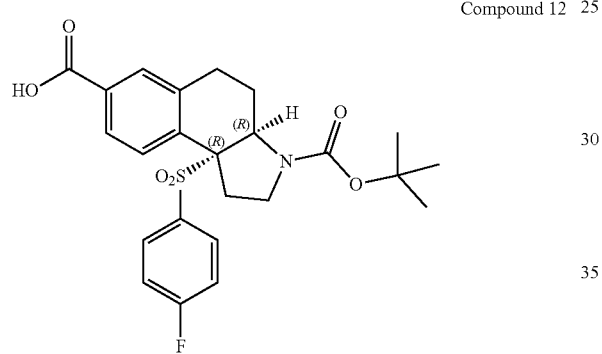

(e) reacting Compound 12 with trifluoromethyltrimethylsilane and N,N'-carbonyldiimidazole in the presence of dichloromethane to obtain Compound 13 of the formula, Compound 13

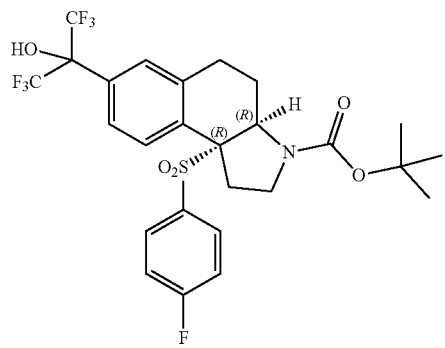

(f) reacting Compound 13 with a fluorinating agent to obtain Compound 14 of the formula, Compound 14

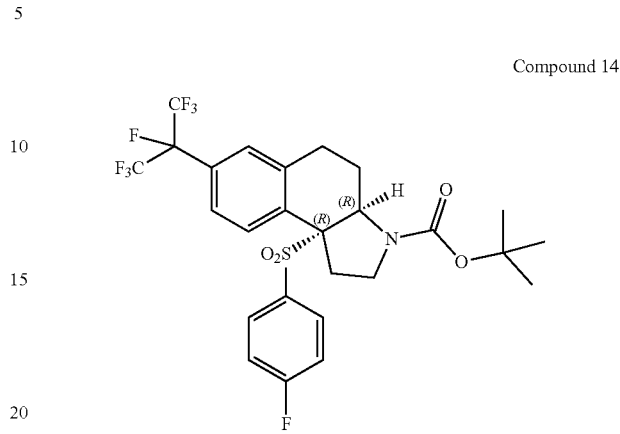

(g) reacting Compound 14 with HCl in dioxane to obtain the Compound of Formula (II).

4. The process according to claim 3, comprising the steps of (a) reacting Compound 8 with Compound 6 in the presence of sodium t-pentoxide and tetrahydrofuran to afford Compound 9, (b) reacting Compound 9 with chlorotrimethylsilane in the presence of a suitable solvent to afford Compound 10, (c) reacting Compound 10 with di-tert-butyl dicarbonate (Boc₂O) in the presence of a NaHCO₃ to afford Compound 11, (d) reacting Compound 11 with iPrMgCl in the presence of CO₂ and tetrahydrofuran to afford Compound 12, (e) reacting Compound 12 with trifluoromethyltrimethylsilane and N,N'-carbonyldiimidazole in the presence of dichloromethane to obtain Compound 13, (f) reacting Compound 13 with (diethylamino) difluorosulfonium tetrafluoroborate in dichloromethane in the presence of tetrabutylammonium fluoride (TBAF) or cesium fluoride (CsF) to obtain Compound 14, and (g) reacting Compound 14 with HCl in dioxane to obtain the Compound of Formula (II).

* * * * *